US012440372B2

(12) United States Patent
Shirpurwala

(10) Patent No.: US 12,440,372 B2
(45) Date of Patent: Oct. 14, 2025

(54) PERSONAL CARE DEVICE

(71) Applicant: Fazle-Imdad Altaf Shirpurwala, Nagpur (IN)

(72) Inventor: Fazle-Imdad Altaf Shirpurwala, Nagpur (IN)

(73) Assignee: Xelfex Inc. (IN)

( * ) Notice: Subject to any disclaimer, the term of this patent is extended or adjusted under 35 U.S.C. 154(b) by 277 days.

(21) Appl. No.: 18/014,612

(22) PCT Filed: Jul. 7, 2021

(86) PCT No.: PCT/IN2021/050660
§ 371 (c)(1),
(2) Date: Jan. 5, 2023

(87) PCT Pub. No.: WO2022/009226
PCT Pub. Date: Jan. 13, 2022

(65) Prior Publication Data

US 2023/0255816 A1 Aug. 17, 2023

(30) Foreign Application Priority Data

Jul. 7, 2020 (IN) .............................. 202021000672

(51) Int. Cl.
*A61F 6/04* (2006.01)

(52) U.S. Cl.
CPC .......... *A61F 6/04* (2013.01); *A61F 2006/044* (2013.01); *A61F 2006/048* (2013.01)

(58) Field of Classification Search
CPC .................. A61F 6/04; A61F 2006/044; A61F 2006/048; A61F 5/453; A61F 5/41; A61F 2005/414; A61F 6/065; A61F 6/02; A61F 2005/411; A61F 6/06; A61F 13/471; A61F 13/82; A61H 19/32; A61H 2201/105; A61H 2201/169; Y10S 128/918
See application file for complete search history.

(56) References Cited

U.S. PATENT DOCUMENTS 5,284,158 A * 2/1994 Mallette .................... A61F 6/04 128/918
6,250,303 B1 * 6/2001 Delaney .................... A61F 6/04 128/918
2012/0181726 A1 * 7/2012 Platt ........................ B29C 41/22 264/254
2018/0000632 A1 * 1/2018 Yun ........................... A61F 6/04

FOREIGN PATENT DOCUMENTS

ES 2590203 T3 * 11/2016 ............... A61F 6/04
KR 20200063597 A * 11/2018 ............... A61F 6/04

* cited by examiner

*Primary Examiner* — Ophelia A Hawthorne
(74) *Attorney, Agent, or Firm* — Christopher Pilling

(57) ABSTRACT

The present invention is directed towards a personal care device. The personal care device comprises a flexible tubular body having an open end, a closed end, an inner surface, and an outer surface. The flexible tubular body is configured to at least partially cover a penis of a user, wherein the open end is configured to be positioned over a shaft of the penis and the closed end is configured to be positioned over a head of the penis, and the inner surface is configured to be contact with the penis. The personal care device also comprises an absorbent region disposed on the inner surface of the flexible tubular body such that the absorbent region is positioned on the shaft of the penis, the absorbent region has an absorbent material bonded with the inner surface.

17 Claims, 10 Drawing Sheets

500

100

PERSONAL CARE DEVICE

FIELD OF THE INVENTION

The present invention relates to a personal care device.

BACKGROUND OF THE INVENTION

Various personal care devices are available for stimulating male and female genitals. While such devices are designed for individual use or personal pleasure, couples often indulge in using such devices together. In this regard, the couples need to be wary as such devices are purely for stimulation and do not have any contraceptive properties.

The market for such devices is flooded with devices for stimulating the female genitals, while the options for such devices for men are limited. Further, most of the devices available for men are mechanized or automated. A male user is always skeptical of the risk associated with introducing their penis in such mechanized/automated devices. Moreover, some of these devices are reusable, which is undesirable at-least from a hygiene perspective. it is well known that masturbation leads to ejaculation of semen. Hence, whether a man uses a device or does the act manually, there is always a considerable amount of cleaning to do. A similar problem is also faced while using contraceptive or personal devices such as condoms, wherein post use of the condom, the condom collects the semen which tends to spread over head and shaft of the penis requiring the user to clean up.

Further, certain men also face the problem of dry or dead skin formation on the penis which is required to be addressed at-least from a hygiene perspective, it has been observed that males are more often hesitant in seeking medical attention when it comes to issues related to the penis, more importantly for issues such as dry or dead skin formation. Considering the sensitive skin of the penis, application of any regular purpose lotion or device for exfoliation is generally not suggested as they might result in itchiness or other serious issues. Therefore, there is a need for a device that can be used for exfoliating the skin, without causing any harm to the penis.

In view of the above, there is a need fir a device which addresses at-least the aforementioned problems.

SUMMARY OF THE INVENTION

In one aspect, the present invention is directed towards a personal care device. The personal care device comprises a flexible tubular body having an open end, a closed end, an inner surface, and an outer surface. The flexible tubular body is configured to at least partially cover a penis, wherein the open end is configured to be positioned over a shaft of the penis and the closed end is configured to be positioned over a head of the penis, and the inner surface is configured to contact with the penis. The personal care device also comprises an absorbent region disposed on the inner surface of the flexible tubular body such that the absorbent region is positioned on the shaft of the penis, the absorbent region has an absorbent material bonded with the inner surface.

In an embodiment of the invention, the absorbent region is positioned adjacent to the open end or the closed end or a center portion of the flexible tubular body.

In still another embodiment of the invention, the absorbent material is coupled with the inner surface by adhesive bonding.

In yet another embodiment of the invention, the absorbent material is coupled with the inner surface by heat bonding.

In a further embodiment of the invention, the absorbent region comprises a tubular absorbent material wrapped around the inner surface of the flexible tubular member, the tubular absorbent material having diameter less than diameter of the personal care device.

In still further embodiment of the invention, the absorbent region comprises plurality of segments of absorbent material disposed in a random configuration.

In yet another embodiment of the invention, the absorbent region comprises of plurality of strips of absorbent material. The plurality of strips of absorbent material are provided in a spaced-apart configuration or an abutting configuration.

In still another embodiment of the invention, the personal care device is a male contraceptive device. The outer surface of the flexible tubular body has a lubricant applied thereon. Further, the outer surface of the flexible tubular body has a patterned surface having ribs or studs or dots or protrusions or a combination thereof.

In still further embodiment of the invention, the inner surface of the flexible tubular body and/or the absorbent material has a patterned surface having ribs or studs or dots or protrusions or a combination thereof. The inner surface of the flexible tubular body also has a lubricant applied thereon.

In still another embodiment of the invention, at least one capsule is provided within the flexible tubular body al the closed end. The capsule is filled with a lubricant, and the capsule is crushable or squeezable for releasing the lubricant.

In yet another embodiment of the invention, the tubular body further comprises a mesh to partition the closed end having the crushable capsules, the mesh prevents movement of the capsule.

In a further embodiment of the invention, the tubular body comprises a seal adjacent to the absorbent region. The seal partitions the flexible tubular body. The seal being a removable seal is made of materials selected from latex, polyvinyl pyrrolidone, polyvinyl alcohol film or paste, and waxes.

In still another embodiment of the invention, the absorbent region has one or more resilient members.

BRIEF DESCRIPTION OF THE DRAWINGS

Reference will be made to embodiments of the invention, examples of which may be illustrated in accompanying figures. These figures are intended to be illustrative, not limiting. Although the invention is generally described in context of these embodiments, it should be understood that it is not intended to limit the scope of the invention to these particular embodiments.

DETAILED DESCRIPTION OF THE INVENTION

The present invention is directed towards a personal care device or a tool for men which aids in stimulating a penis and/or creating a physical barrier during intercourse between a user and a partner. The personal care device can also be used for cleaning or exfoliation of a shaft of the penis.

Figure 1:
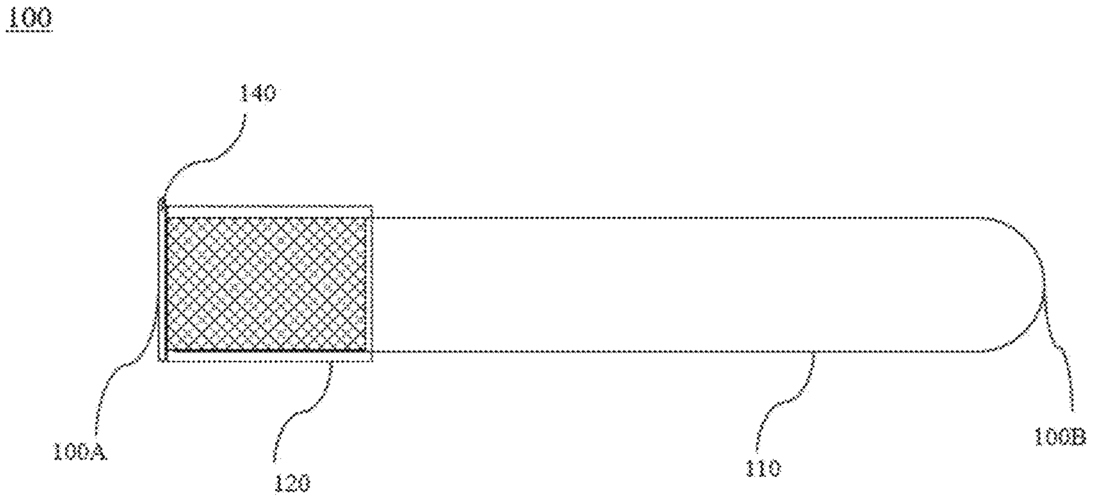
FIG. 1 shows a sectional view of a personal care device in accordance with an embodiment of the invention.

FIG. 1 shows a personal care device 100 for stimulating a penis in accordance with an embodiment of the invention. As shown, the personal care device comprises of a flexible tubular body 110 and an absorbent region 120. The flexible tubular body enables the personal care device to be worn and fitted onto the penis of a user, and the absorbent region aids in wiping/cleaning fluids present/secreted on or around the penis. In this regard, size and diameter of the tubular body may be varied so as to fit the penis.

The flexible tubular body extends from an open end 100A to a closed end 100B. The flexible tubular body is configured to at least partially cover the penis whereby the inner surface is configured to be in contact with the penis, and the open end is configured to be positioned over a shaft of the penis and the closed end is configured to be position over a head of the penis.

Further, the flexible tubular body has an inner surface and an outer surface. In an embodiment of the invention, the absorbent region is disposed on the inner surface of the flexible tubular body such that when the personal care device is worn by the user the absorbent region is positioned on the shaft of the penis. As shown, the absorbent region can be provided adjacent to the open end of the flexible tubular body. In an embodiment, the absorbent region can be positioned adjacent to a center portion of the flexible tubular body. In another embodiment, the absorbent region can be positioned adjacent to the closed end of the flexible tubular body.

In one embodiment, the inner surface of the flexible tubular body is lubricated for lubricating the penis. In this regard, the absorbent region is dry and does not have lubricants applied thereon.

The absorbent region has an absorbent material bonded with the inner surface of the flexible tubular body. The absorbent material is coupled with the inner surface by adhesive bonding. Suitable adhesives for this purpose have been described hereinbelow.

In another embodiment, the absorbent material is coupled with the inner surface by heat bonding. In this regard, the absorbent material and/or flexible tubular body forming material can be heated sufficiently or closer to their melting point for coupling/fusion to occur. The choice of a suitable temperature range for this purpose depends on the type of absorbent material and/or flexible tubular body forming material.

The absorbent region/material can be provided on the inner surface in different configurations. By way of example, the absorbent region can have a sheet or tubular absorbent material or have plurality of segments of absorbent material or plurality of strips of absorbent material. In this regard, variations of shape and structure of the different configurations is well within the scope of the present invention.

In an embodiment, the different configurations of the absorbent material take up the shape of the flexible tubular body upon coupling thereto. In another embodiment, the different configurations of the absorbent material can have a tubular structure to be easily adapted on the inner surface of the flexible tubular material.

Figure 2:
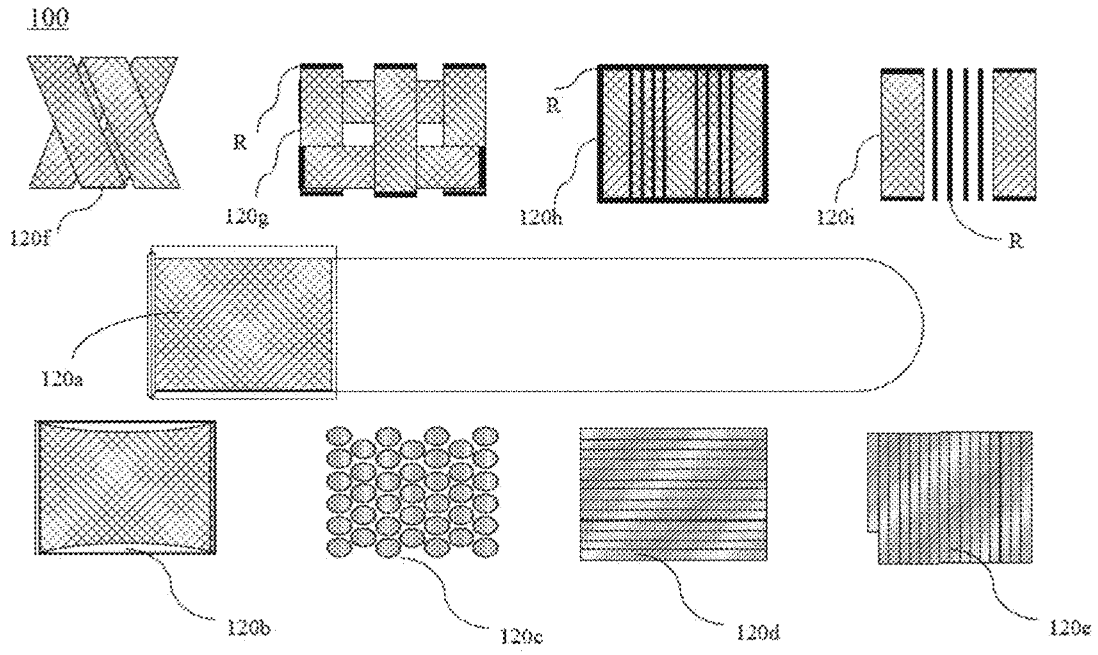
FIG. 2 shows sectional view of various embodiments of an absorbent region of the personal care device.

As shown in FIG. 2, an absorbent region 120*a* has a sheet of absorbent material. The sheet is wrapped around the inner surface of the flexible tubular body. The sheet is bonded with the inner surface of the flexible tubular body to form a layer of the absorbent material.

The absorbent region 120*a* is also advantageous in terms of manufacturing the personal care device. For instance, the sheet of absorbent material can be placed on a conveyor belt or a wheel such that it comes in contact with a mandrel which is pre-loaded with the flexible tubular body forming material. The sheet is then coupled with the inner surface by an adhesive which can be applied on the sheet itself or the mandrel.

In an embodiment, an absorbent region 120*b* has a tubular absorbent material with diameter less than a diameter of the personal care device. This prevents the personal care device from slipping over the penis post ejaculation. In such a scenario, the tubular absorbent material folds over the flexible tubular body and forms a barrier, thereby resisting the slipping off of the personal care device. In an embodiment, the tubular absorbent material folds over itself, thereby increasing in thickness and enhancing the grip on the penis for effectively cleaning any semen. The tubular absorbent material further prevents the lubricant from escaping the inner surface as well preventing any semen from escaping the flexible tubular body. Moreover, in the event of the penis going flaccid, the tubular absorbent material helps the personal care device to grip the penis which has reduced in diameter due to flaccid state. Furthermore, the tubular absorbent material also provides for a better fitting over the shaft of the penis, thereby providing an enhanced user experience and cleaning or exfoliation of the shaft of the penis.

The absorbent region 120*b* is also advantageous in terms of manufacturing the personal care device. For instance, the tubular absorbent material can be provided on a hollow solid tube and placed on a mandrel which is pre-loaded with the flexible tubular body forming material. The tubular absorbent material is then slid over the mandrel and is coupled by using suitable coupling agent or heating. In an embodiment, the tubular absorbent material is coupled with the inner surface by coupling both open ends of the tubular absorbent material such that a middle section of the tubular absorbent material remains suspended. This forms multiple folds of the tubular absorbent material with each fold overlapping the other. The multiples folds aid in better grip of the penis.

Further, an absorbent region 120*c* has plurality of segments provided in a random configuration, whereby the segments are adjacent to each other. While the segments illustrated are circular, different shapes of the segment can be embedded. Moreover, the size and thickness of the segments can be appropriately selected and therefore the present invention is not limited by the same. Each segment is embedded with the inner surface of the flexible tubular body via an adhesive. The segments in the configuration illustrated render a textured surface. Advantageously, the plurality of segments allow for a thinner absorbent material to be used in the personal care device. In such a scenario, the plurality of segments would not possess elasticity and rely on the flexible tubular body forming material instead.

The personal care device having the absorbent region 120*c* on the inner surface of the flexible tubular body can be advantageously manufactured. For instance, the plurality of segments in a tiny ball-like shape can be placed on a sliding container adjacent to a mandrel which is pre-loaded with the flexible tubular body forming material. The mandrel rotates at a sufficient speed while the plurality of segments is allowed to fall on the rolling mandrel. In an embodiment, the mandrel can have an adhesive applied thereupon prior to providing the plurality of segments. In another embodiment, the adhesive can be applied after the plurality of segments have been provided on the mandrel.

An absorbent region 120*d* with plurality of strips is also illustrated. The strips as shown are provided in an abutting configuration. The plurality of strips is wrapped around the inner surface of the flexible tubular body. The absorbent region 120*d* with plurality of strips running parallel to a length of the personal care device allow for a thinner absorbent material to be used. In such a scenario, the plurality of strips would not possess elasticity and rely on the tubular body forming material instead.

The personal care device having the absorbent region 120*d* on the inner surface of the flexible tubular body can be advantageously manufactured. For instance, the plurality of strips can be placed on a conveyor belt running under a mandrel which is pre-loaded with the flexible tubular body forming material. The mandrel is rotated at a sufficient speed to allow the plurality of strips with sufficient time to adapt onto the mandrel. In an embodiment, an adhesive is applied on the mandrel and thereafter the plurality of strips is adapted to the mandrel. In another embodiment, the adhesive can be applied after adapting the mandrel with the plurality of strips.

Furthermore, the absorbent region 120*e* with plurality of strips can be provided in an abutting configuration, Each strip is embedded with the inner surface of the flexible tubular body via an adhesive. The absorbent region 120*e* with plurality of strips running parallel to a circumference of the personal care device allow for a faster and quicker route for manufacturing the personal care device.

The absorbent region 120*e* can be advantageously provided on the inner surface of the flexible tubular body. The absorbent material as plurality of strips is selected in a manner as to provide elasticity to the flexible tubular body, thereby aiding in easily adaptation on the shaft of the penis. The plurality of strips can be obtained from a rotating spindle. A mandrel which is pre-loaded with the flexible tubular body forming material and rotates with a sufficient speed to allow the plurality of strips to be easily adapted thereto, is placed adjacent to the rotating spindle. The plurality of strips from the rotating spindle are then allowed to be adapted on the rotating mandrel. In an embodiment, an adhesive is applied on the mandrel and thereafter the plurality of strips is adapted thereto. In another embodiment, the adhesive is applied after the plurality of strips is adapted to the mandrel.

Further, as shown, the absorbent region 120*f*, 120*g* with plurality of strips can be provided in an overlapping configuration. The plurality of strips allows for the personal care device to effectively and efficiently clean the shaft of the penis by putting in use all the strips once the semen is in contact with the innermost or first strip. Alternately, the absorbent region with plurality of strips can be provided in a spaced apart configuration.

Furthermore, in an embodiment, absorbent region can have one or more resilient members along with the absorbent material. For example, absorbent region 120*g*, 120*h*, 120*i* have one or more resilient members R. The resilient member can be strips or rings spaced apart as shown in the figure for providing additional grip to the flexible tubular body. In an embodiment, the resilient material includes rubber and similar elastomers. The absorbent region 120*g* allows for a mesh kind of arrangement with gaps having absorbent materials to absorb the semen while the personal care device is being removed. The absorbent region 120*h* along with the resilient material provides for a better grip on the shaft. Further, the resilient members provided on the absorbent region also prevents the semen from trickling towards the open end. Also, while removing the device, the resilient members pushes the semen towards the closed end of the flexible tubular body. For example, a first strip towards the closed end prevents the semen and lubricant from trickling down and also pushes the semen and lubricant towards the closed end while removing the personal care device. A second strip towards the open end remains dry due to the first strip absorbing most of the semen and lubricant. The second strip cleans the remaining semen and lubricant on the shaft of the penis while removing the personal care device.

In an embodiment, the inner surface of the flexible tubular body and/or the absorbent material has a patterned surface. The patterned surface can have ribs or studs or dots or protrusions or a combination thereof. In an embodiment, the protrusions can have any shape or geometry, for instance, rhombus, square, diamond, polygonal, or a combination thereof. The patterned surface aids in stimulation and can also be used for exfoliating any dry or dead skin that may have formed on the penis.

Figure 3:
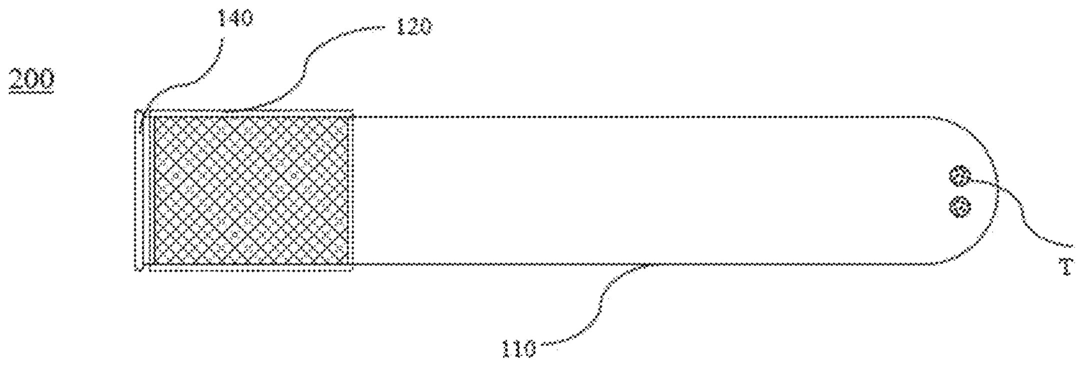
FIG. 3 shows a sectional view of a personal care device in accordance with an embodiment of the invention.

FIG. 3 shows a personal care device 200 according to an embodiment of the invention. The personal care device is similar to the personal care device discussed hereinbefore and further comprises at-least one capsule T within the flexible tubular body. The capsule has a shell which holds oils or lubricants. The capsule is crushable/squeezable such that upon crushing/squeezing the capsule the shell breaks/cracks/squeezes, thereby allowing the lubricant to release from the shell/capsule within the flexible tubular body. Further, the capsule is preferably provided near the closed end such that upon use; the capsule releases the lubricant which trickles on to the penis. The lubricant further enhances user experience. The capsule can be adapted to the flexible tubular body by an adhesive.

Figure 4A:
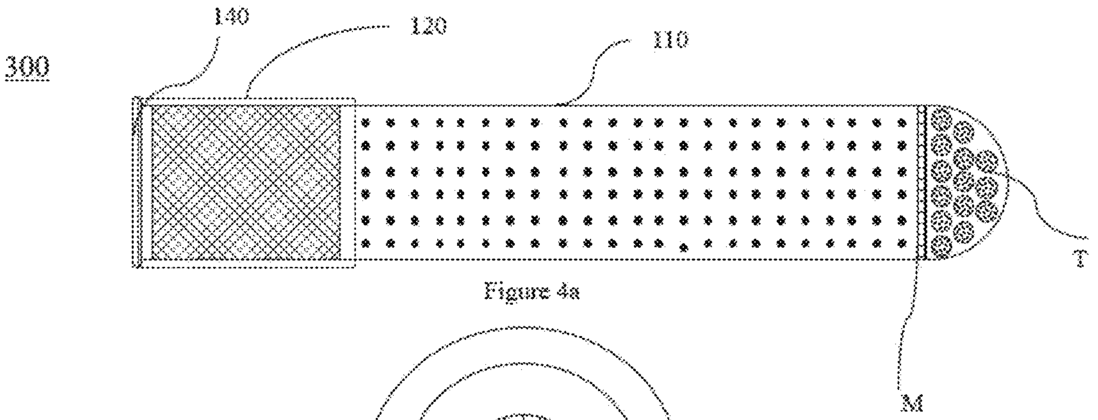
FIGS. 4*a* and 4*b* show sectional views of a personal care device in accordance with an embodiment of the invention.
Figure 4B:
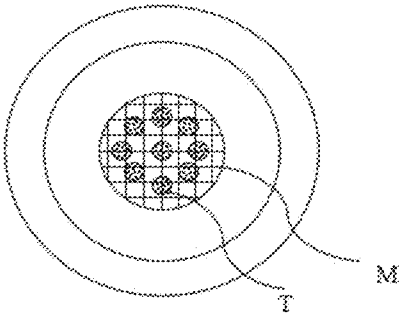

Further, as shown in FIGS. 4*a* and 4*b*, the personal care device 300. The personal care device is similar to the personal care device discussed hereinbefore and comprises a mesh or a net M. The mesh or net is provided adjacent to the closed end for preventing movement of the capsules. However, the mesh/net allows the lubricant of the capsules to flow through, thereby preventing shell of the capsule from moving over the shaft and avoiding any discomfort to the user.

Figure 5:
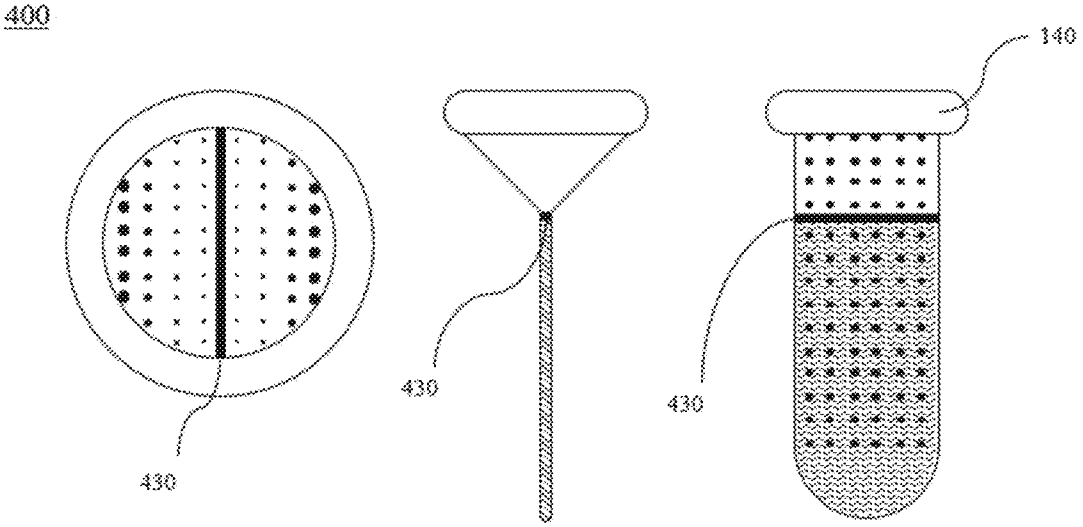
FIG. 5 shows a sectional view of a personal care device in accordance with an embodiment of the invention.

FIG. 5 shows a personal care device 400 in accordance with an embodiment of the invention. The personal care device is similar to the personal care device discussed hereinbefore and comprises a seal 430 to partition the flexible tubular body. The seal is provided along inner surface of the flexible tubular body. In an embodiment, the seal is provided towards the center portion or closed end of the flexible tubular body. In another embodiment, the seal is a removable seal made of materials selected from latex, polyvinyl pyrrolidone, polyvinyl alcohol film or paste, and waxes. The application of seal results in inner walls of the flexible tubular body to stick due to the presence of lubricant on the inner surface. This results in the flexible tubular body becoming flat, thereby allowing for an easier packaging of the personal care device as well as preventing the lubricant from escaping. However, the walls are separable once the seal is broken by the user, for instance by pulling apart the open end of the personal care device.

Figure 6:
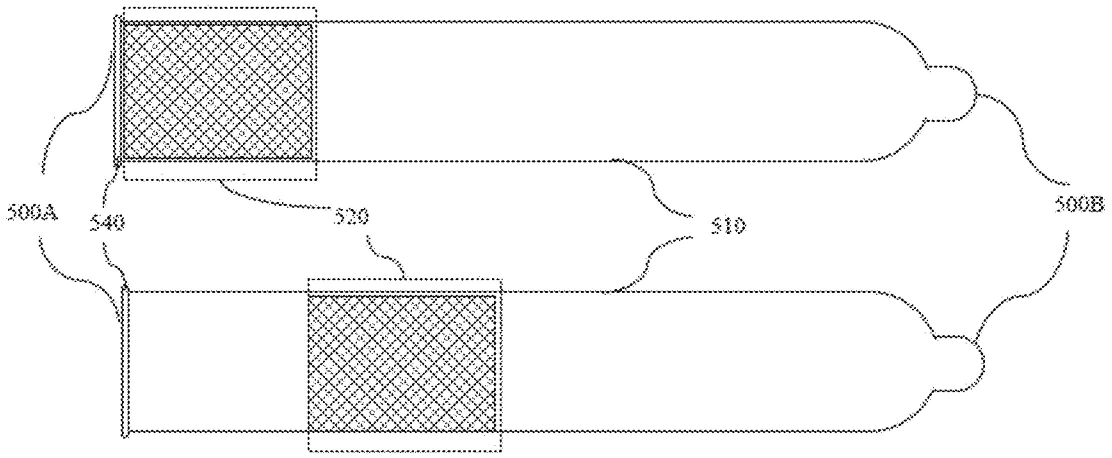
FIG. 6 shows a sectional view of a personal care device in accordance with an embodiment of the invention.

FIG. 6 shows a personal care device 500 for creating a physical barrier between a user and a partner during intercourse in accordance with an embodiment of the invention. As shown, the personal care device comprises of a flexible tubular body 510 and an absorbent region 520. The flexible tubular body enables the personal care device to be worn and fitted onto a penis of the user, and the absorbent region aids in wiping/cleaning fluids present/secreted on or around the penis. In this regard, size and diameter of the tubular body may be varied so as to fit the penis.

The flexible tubular body extends from an open end 500A to a closed end 500B. The flexible tubular body is configured to at least partially cover the penis whereby the inner surface is configured to be in contact with the penis, and the open end is configured to be positioned over a shaft of the penis and the closed end is configured to be position over a head of the penis.

Further, the flexible tubular body has an inner surface and an outer surface. In an embodiment of the invention, the absorbent region is disposed on the inner surface of the flexible tubular body such that when the personal care device is worn by the user the absorbent region is positioned on the shaft of the penis. As shown, the absorbent region can be provided adjacent to the open end of the flexible tubular body or positioned adjacent to the portion center of the flexible tubular body.

The absorbent region has an absorbent material bonded with the inner surface of the flexible tubular body. The absorbent material is coupled with the inner surface by adhesive bonding. Suitable adhesives for this purpose have been described hereinbelow.

In another embodiment, the absorbent material is coupled with the inner surface by heat bonding. In this regard, the absorbent material and/or flexible tubular body forming material can be heated sufficiently or closer to their melting point for coupling/fusion to occur. The choice of a suitable temperature range for this purpose depends on the type of absorbent material and/or flexible tubular body forming material.

The absorbent region/material can be provided on the inner surface in different configurations. By way of example, the absorbent region can have a sheet or tubular absorbent material or have plurality of segments of absorbent material or plurality of strips of absorbent material.

In an embodiment, the different configurations of the absorbent material take up the shape of the flexible tubular body upon coupling thereto. In another embodiment, the different configurations of the absorbent material can have a tubular structure to be easily adapted on the inner surface of the flexible tubular material.

Figure 7:
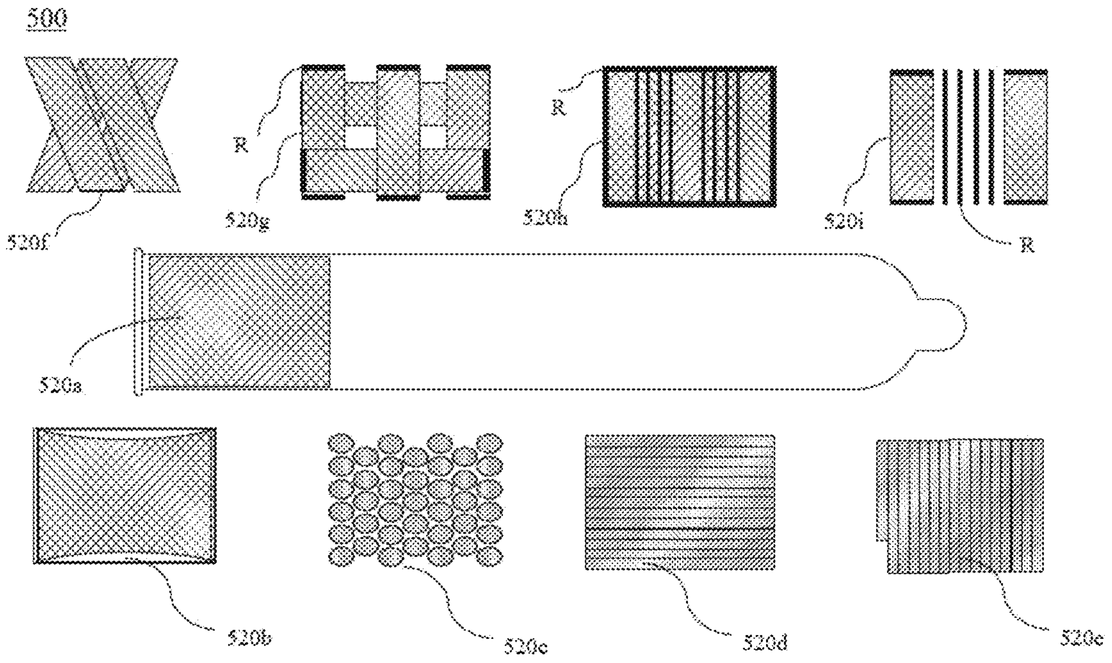
FIG. 7 shows various embodiments of an absorbent region of the personal care device.

As shown in FIG. 7. an absorbent region 520*a* has a sheet of absorbent material. The sheet is wrapped around the inner surface of the flexible tubular body. The sheet is bonded with the inner surface of the flexible tubular body to form a layer of the absorbent material.

The absorbent region 520*a* is also advantageous in terms of manufacturing the personal care device. For instance, the sheet of absorbent material can be placed on a conveyor belt or a wheel such that it conies in contact with a mandrel which is pre-loaded with the flexible tubular body forming material. The sheet is then coupled with the inner surface by an adhesive which can be applied on the sheet itself or the mandrel.

In an embodiment, an absorbent region 520*b* has a tubular absorbent material with diameter less than a diameter of the personal care device. This prevents the personal care device from slipping over the penis post ejaculation. In such a scenario, the tubular absorbent material folds over the flexible tubular body and forms a barrier, thereby resisting the slipping off of the personal care device. The tubular absorbent material further prevents the lubricant from escaping the inner surface. Moreover, in the event of the penis going flaccid, the tubular absorbent material helps the personal care device to grip the penis which has reduced in diameter due to flaccid state. Furthermore, the tubular absorbent material also provides for a better fitting over the shaft of the penis, thereby providing an enhanced user experience and cleaning or exfoliation of the shaft of the penis.

The absorbent region 520*b* is also advantageous in terms of manufacturing the personal care device. For instance, the tubular absorbent material can be provided on a hollow solid tube and placed on a mandrel which is pre-loaded with the flexible tubular body forming material. The tubular absorbent material is then slid over the mandrel and is coupled by using suitable coupling agent or heating. In an embodiment, the tubular absorbent material is coupled with the inner surface by coupling both open ends of the tubular absorbent material such that a middle section of the tubular absorbent material remains suspended. This forms multiple folds of the tubular absorbent material with each fold overlapping the other. The multiples folds aid in better grip of the penis.

Further, an absorbent region 520*c*, has plurality of segments provided in a random configuration, whereby the segments are adjacent to each other. While the segments illustrated are circular, different shapes of the segment can be embedded. Moreover, the size and thickness of the segments can be appropriately selected and therefore the present invention is not limited by the same. Each segment is embedded with the inner surface of the flexible tubular body via an adhesive. The segments in the configuration illustrated render a textured surface. Advantageously, the plurality of segments allow for a thinner absorbent material to be used in the personal care device. In such a scenario, the plurality of segments would not possess elasticity and rely on the flexible tubular body forming material instead.

The personal care device having the absorbent region 520*c* on the inner surface of the flexible tubular body can be advantageously manufactured. For instance, the plurality of segments in a tiny ball-like shape can be placed on a sliding container adjacent to a mandrel which is pre-loaded with the flexible tubular body forming material. The mandrel rotates at a sufficient speed while the plurality of segments is allowed to fall on the rolling mandrel. In an embodiment, the mandrel can have an adhesive applied thereupon prior to providing the plurality of segments. In another embodiment, the adhesive can be applied after the plurality of segments have been provided on the mandrel.

An absorbent region 520*d* with plurality of strips is also illustrated. The strips as shown are provided in an abutting configuration. The plurality of strips is wrapped around the inner surface of the flexible tubular body. The absorbent region 520*d* with plurality of strips running parallel to a length of the personal care device allow for a thinner absorbent material to be used. In such a scenario, the plurality of strips would not possess elasticity and rely on the tubular body forming material instead.

The personal care device having the absorbent region 520*d* on the inner surface of the flexible tubular body can be advantageously manufactured. For instance, the plurality of strips can be placed on a conveyor belt running under a mandrel which is pre-loaded with the flexible tubular body forming material. The mandrel is rotated at a sufficient speed to allow the plurality of strips with sufficient time to adapt onto the mandrel. In an embodiment, an adhesive is applied on the mandrel and thereafter the plurality of strips is adapted to the mandrel. In another embodiment, the adhesive can be applied after adapting the mandrel with the plurality of strips.

Furthermore, the absorbent region 520*e* with plurality of strips can be provided in an abutting configuration. Each strip is embedded with the inner surface of the flexible tubular body via an adhesive. The absorbent region 520*e* with plurality of strips running parallel to a circumference of the personal care device allow for a faster and quicker route for manufacturing the personal care device.

The absorbent region 520*e* can be advantageously provided on the inner surface of the flexible tubular body. The absorbent material as plurality of strips is selected in a manner as to provide elasticity to the flexible tubular body, thereby aiding in easily adaptation on the shaft of the penis. The plurality of strips can be obtained from a rotating spindle. A mandrel which is pre-loaded with the flexible tubular body forming material and rotates with a sufficient speed to allow the plurality of strips to be easily adapted thereto, is placed adjacent to the rotating spindle. The plurality of strips from the rotating spindle are then allowed to he adapted on the rotating mandrel. In an embodiment, an adhesive is applied on the mandrel and thereafter the plurality of strips is adapted thereto. In another embodiment, the adhesive is applied after the plurality of strips is adapted to the mandrel.

Further, as shown, the absorbent region 520*f*, 520*g* with plurality of strips can be provided in an overlapping configuration. The plurality of strips allows for the personal care device to effectively and efficiently clean the shaft of the penis by putting in use all the strips once the semen is in contact with the innermost or first strip. Alternately, the absorbent region with plurality of strips can be provided in a spaced apart configuration can also be provided.

Furthermore, in an embodiment, the absorbent region can have one or more resilient members along with the absorbent material. For example, absorbent region 520*g*, 520*h*, 520*i* have one or more resilient members R. The resilient member can be strips or rings spaced apart as shown in the figure for providing additional grip to the flexible tubular body. In an embodiment, the resilient material includes rubber and similar elastomers. The absorbent region 520*g* allows for a mesh kind of arrangement thereby creating gaps for the parts that are behind to absorb the semen while the personal care device is being removed. The absorbent region 520*h* along with the resilient material provides for a better grip on the shaft. The absorbent region 520*i* with plurality of strips and one or more resilient materials performs a dual function. A first strip towards the closed end prevents the semen and lubricant from escaping the flexible tubular body and in fact pushes the semen and lubricant towards the closed end. A second strip towards the open end remains dry due to the first strip absorbing most of-the semen and lubricant. The second strip cleans the remaining semen and lubricant on the shaft of the penis while removing the personal care device Further, the outer surface of the flexible tubular body has lubrication and/or has a patterned surface. The lubrication makes intercourse easier and patterned surface stimulates the partner. The patterned surface can have ribs or studs or dots or protrusions or a combination thereof. The patterned surface aids in stimulation of the vagina during intercourse. In an embodiment, the protrusions can have any shape or geometry, for instance, rhombus, square, diamond, polygonal, or a combination thereof.

In the embodiments discussed hereinabove, the open end of the personal care device also includes an integral bead (rolled ring) 140, 540. The integral bead is an extension of the flexible tubular body to hold the personal care device on the shaft of the penis.

Figure 9:
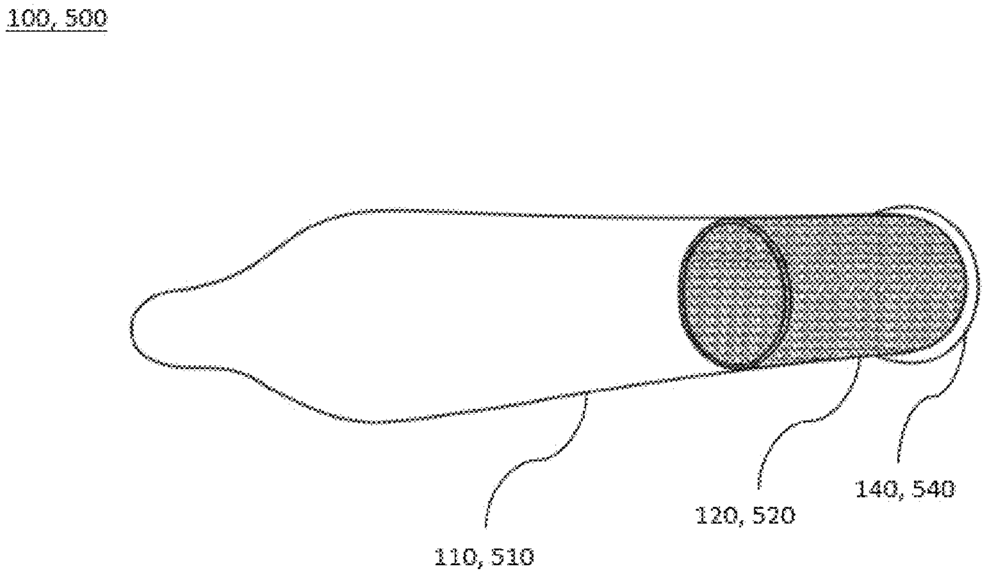
FIG. 9 shows a perspective view of a personal care device in a packed state in accordance with an embodiment of the invention.
Figure 10:
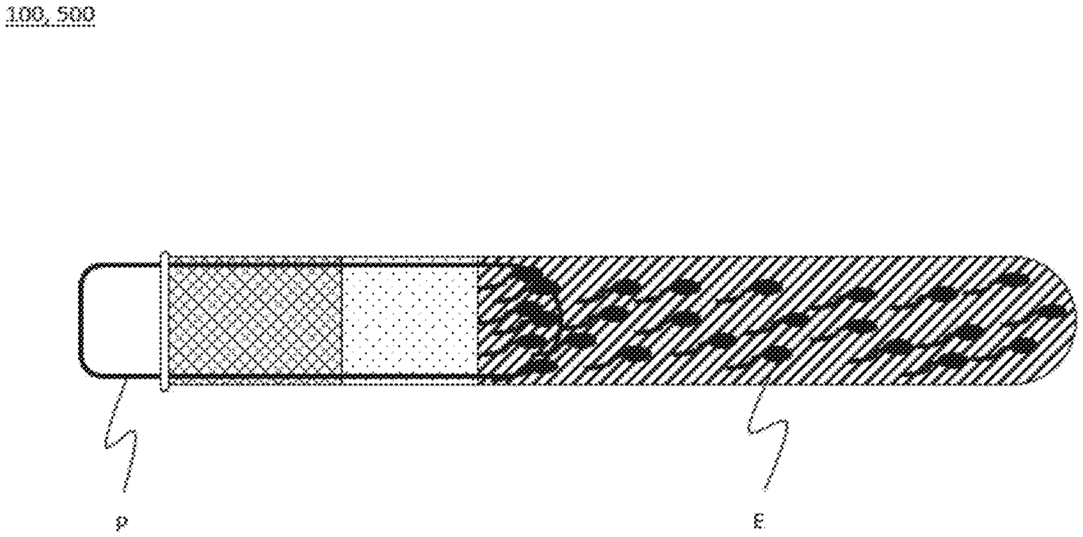
FIG. 10 shows an illustrative representation of the personal care device after use.

FIG. 9 shows a perspective view of a personal care device 100, 500 in accordance with an embodiment of the invention. As discussed hereinabove, the personal care device can be used as a tool to aid stimulation of the penis or can be used as a barrier between the user and a partner of the user for preventing any infections or any unplanned and undesirable consequences. In use, the personal care device 100, 500 is worn over the penis or penis P as illustrated in FIG. 10. The flexible tubular body allows the personal care device to be easily accommodated over the penis whereby the tubular body conforms with the shape of the penis. Once on the penis, the penis simply has to be stimulated or stroked. In case the user is using the personal care device for stimulation of the penis on his own, the lubricant on inner surface or lubricant released from the capsule enhances the user experience, while the absorbent material ensures the lubricant does not escape the flexible tubular body. Upon stimulation, when a user ejaculates, the flexible tubular body collects the semen as shown in FIG. 10 avoiding any spillage to surrounding areas and keeping it within the flexible tubular body. In case the user is using the personal care device as a condom with his partner, the device provides a physical barrier between the user and a partner of the user, thereby preventing any infections or any unplanned and undesirable consequences. Post ejaculation, the user has to remove the tubular member during which the absorbent material comes in contact with various parts of the penis either on its own or may require a little bit of maneuvering which helps in cleaning the penis. The advantage of the device is exhibited herein as semen is collected in the device, and the user can wipe his organ through the absorbent material while removing/withdrawing the organ from the device.

In the embodiments discussed hereinabove, the flexible tubular body is formed from latex, rubber, urethane polymers and the like. Further, the absorbent material is a liquid absorbent material and can be selected from natural or synthetic fabric-based materials or porous materials. The fabric can be woven fabric or resilient fabric material. In an embodiment, the absorbent material can be selected in a manner that the absorbent region is flexible. The absorbent material can also contain solvents for improving the cleaning. In an embodiment, the absorbent material has a patterned surface, The patterned surface can be any random pattern as per requirement. The said pattern ensures that body fluids are absorbed and also not allowed trickle down or escape which otherwise would happen if there was no pattern or in the case of straight lines.

Further, in the embodiments discussed herein above, the adhesive is selected from liquid latex, polyurethane glue, polyvinyl chloride glue, and neoprene glue. In another embodiment, the adhesive is selected from liquid latex, polyurethane glue, and neoprene glue, can be selected from liquid latex, polyurethane glue, polyvinyl chloride glue, polychloroprene glue, nairitic glue, and neoprene glue. Adhesives such as perchlorovinyl, phenol-formaldehyde, and epoxy in organic solvents can also be used as suitable bonding material.

Figure 8:
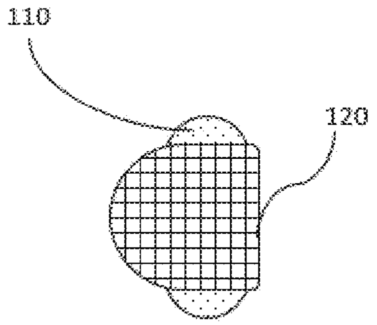
FIG. 8 shows the personal care device in a packed state in accordance with an embodiment of the invention.

FIG. 8 shows the personal care device in a packed configuration. In the packed configuration, the absorbent region is rolled, and the flexible tubular body is wrapped around the rolled absorbent region enabling the personal care device to be reduced to a compact size in order to be packed and/or stored. To use, the tubular body is to be unrolled and as shown in FIG. 10, the tubular body can be at least partially unrolled over the penis and after ejaculation can further be un-rolled to reveal the absorbent material towards the open end.

In an embodiment, the present invention provides a method for forming a personal care device. The method starts by providing an absorbent material around a mandrel. The mandrel is a glass, porcelain or ceramic mandrel extending from a first end to a second end. In one embodiment of the invention, at the second end, the mandrel has a bulbous shape or any other shape. The absorbent material is wrapped adjacent to the first end of the mandrel such that the absorbent material takes a tubular shape with open ends. Subsequent to wrapping the absorbent material around the mandrel, the adhesive is applied on the absorbent material and the absorbent material is coupled with the inner surface of a flexible tubular body. In this regard, the flexible tubular body may be preformed or a flexible material forming the flexible tubular body can be fused with the absorbent material by dipping the mandrel into a bath comprising the flexible material in viscous form or by spraying flexible material around the mandrel. Thereafter, the flexible material is allowed to be dried and cured. The personal care device thus formed has a tubular body comprising of absorbent material and a flexible tubular body having bulbous shape. In an embodiment of the invention, the mandrel is coated with a lubricant whereby the lubricant transfers to inner-side of the flexible material formed on the mandrel. Accordingly, inner-side of the flexible material is lubricated. In an alternate embodiment, lubricant can be applied on the outer surface of the flexible tubular body subsequent to drying.

Advantageously, the present invention provides a personal care device which aids in stimulation, contraception, and also has features to clean-up. In addition to providing a better experience to the user, the personal care device also aids in prevention of sexual transmitted diseases (STD) and unwanted pregnancies. The personal care device can also be used for cleaning or exfoliation of the shaft of the penis.

The foregoing description of the invention has been set merely to illustrate the invention and is not intended to be limiting. Since the modifications of the disclosed embodiments incorporating the spirit and substance of the invention may occur to the person skilled in the art, the invention should be construed to include everything within the scope of the disclosure.

The invention claimed is:

1. A personal care device, comprising:

a flexible tubular body having an open end, a closed end, an inner surface, and an outer surface, the flexible tubular body configured to at least partially cover a penis, wherein the open end is configured to be positioned over a shaft of the penis and the closed end is configured to be positioned over a head of the penis, and the inner surface is configured to contact with the penis; and, an absorbent region disposed on the inner surface of the flexible tubular body such that the absorbent region is positioned on the shaft of the penis, the absorbent region has an absorbent material bonded with the inner surface;

wherein the absorbent region comprises a tubular absorbent material wrapped around the inner surface of the flexible tubular member, the tubular absorbent material having diameter less than diameter of the personal care device.

2. The personal care device as claimed claim 1, wherein the personal care device is a male contraceptive device.

3. The personal care device as claimed in claim 2, wherein the outer surface of the flexible tubular body has a lubricant applied thereon.

4. The personal care device as claimed in claim 2, wherein the outer surface of the flexible tubular body has a patterned surface having ribs or studs or dots or protrusions or a combination thereof.

5. The personal care device as claimed in claim 1, wherein the absorbent region comprises a plurality of strips of absorbent material.

6. The personal care device as claimed in claim 5, wherein the plurality of strips of absorbent material are provided in a spaced-apart configuration or in an abutting configuration.

7. The personal care device as claimed in claim 1, wherein the absorbent region is positioned adjacent to the open end or the closed end or a center portion of the flexible tubular body.

8. The personal care device as claimed in claim 1, wherein the absorbent material is coupled with the inner surface by adhesive bonding.

9. The personal care device as claimed in claim 1, wherein the absorbent material is coupled with the inner surface by heat bonding.

10. The personal care device as claimed in claim 1, wherein the absorbent region comprises a plurality of segments of absorbent material disposed in a random configuration.

11. The personal care device as claimed in claim 1, wherein the inner surface of the flexible tubular body and/or the absorbent material has a patterned surface having ribs or studs or dots or protrusions or a combination thereof.

12. The personal care device as claimed in claim 1, wherein the inner surface of the flexible tubular body has a lubricant applied thereon.

13. The personal care device as claimed in claim 1, wherein at least one capsule is provided within the flexible tubular body at the closed end, the capsule filled with a lubricant, and the capsule is crushable or squeezable for releasing the lubricant.

14. The personal care device as claimed in claim 1, wherein the tubular body further comprises a mesh to partition the closed end having the crushable capsules, the mesh prevents movement of the capsule.

15. The personal care device as claimed in claim 1, wherein the tubular body comprising a seal adjacent to the absorbent region, the seal partitions the flexible tubular body, the seal being a removable seal made of materials selected from latex, polyvinyl pyrrolidone, polyvinyl alcohol film or paste, and waxes.

16. The personal care device as claimed in claim 1, wherein the absorbent region has one or more resilient members.

17. A personal care device, comprising:

a flexible tubular body having an open end, a closed end, an inner surface, and an outer surface, the flexible tubular body configured to at least partially cover a penis, wherein the open end is configured to be positioned over a shaft of the penis and the closed end is configured to be positioned over a head of the penis, and the inner surface is configured to contact with the penis; and, an absorbent region disposed on the inner surface of the flexible tubular body such that the absorbent region is positioned on the shaft of the penis, the absorbent region has an absorbent material bonded with the inner surface;

a seal adjacent to the absorbent region, the seal partitions the flexible tubular body, the seal being a removable seal made of materials selected from latex, polyvinyl pyrrolidone, polyvinyl alcohol film or paste, and waxes.

* * * * *